United States Patent
Takei et al.

(10) Patent No.: US 11,198,106 B2
(45) Date of Patent: Dec. 14, 2021

(54) METHOD FOR PRODUCING MICROCAPSULES OR BEADS

(71) Applicant: KAGOSHIMA UNIVERSITY, Kagoshima (JP)

(72) Inventors: Takayuki Takei, Kagoshima (JP); Masahiro Yoshida, Kagoshima (JP); Yoshihiro Ohzuno, Kagoshima (JP); Gen Hayase, Ibaraki (JP)

(73) Assignee: KAGOSHIMA UNIVERSITY, Kagoshima (JP)

( * ) Notice: Subject to any disclaimer, the term of this patent is extended or adjusted under 35 U.S.C. 154(b) by 0 days.

(21) Appl. No.: 16/640,588

(22) PCT Filed: Aug. 8, 2018

(86) PCT No.: PCT/JP2018/029810
§ 371 (c)(1),
(2) Date: Feb. 20, 2020

(87) PCT Pub. No.: WO2019/039292
PCT Pub. Date: Feb. 28, 2019

(65) Prior Publication Data
US 2020/0171454 A1 Jun. 4, 2020

(30) Foreign Application Priority Data
Aug. 24, 2017 (JP) .............................. JP2017-161323

(51) Int. Cl.
*B01J 13/14* (2006.01)
(52) U.S. Cl.
CPC ................................... *B01J 13/14* (2013.01)

(58) Field of Classification Search
CPC ........................................................ B01J 13/14
See application file for complete search history.

(56) References Cited

U.S. PATENT DOCUMENTS

| | | |
|---|---|---|
| 4,233,178 A | 11/1980 | Fuchigami |
| 4,409,156 A | 10/1983 | Hoshi et al. |
| 2013/0122070 A1 | 5/2013 | Barnett et al. |

FOREIGN PATENT DOCUMENTS

| | | |
|---|---|---|
| JP | S5449984 A | 4/1979 |
| JP | S5651238 A | 5/1981 |

(Continued)

OTHER PUBLICATIONS

International Search Report for Corresponding International Application No. PCT/JP2018/029810 (2 Pages) (dated Nov. 6, 2018).

*Primary Examiner* — Tabatha L Penny
(74) *Attorney, Agent, or Firm* — Lucas & Mercanti, LLP

(57) ABSTRACT

An object of the invention is to provide a method for producing a capsule or microbead having high encapsulation efficiency of an encapsulated substance, high production efficiency, and high versatility. The invention relates to a method for producing a microcapsule or microbead, comprising: a step of disposing a monomer droplet or polymer droplet containing a substance to be encapsulated, which has a surface coated with a plurality of solid fine particles, on a flat surface; and a step of solidifying the monomer droplet or polymer droplet disposed on the flat surface in a gas phase so as to form an outer shell of a capsule or microbead, thereby forming a region enclosed by the outer shell, wherein the substance is encapsulated in the region.

3 Claims, 6 Drawing Sheets

(56) References Cited

FOREIGN PATENT DOCUMENTS

| | | | |
|---|---|---|---|
| JP | H02169026 | * | 6/1990 |
| JP | 2004250367 A | | 9/2004 |
| JP | 2009292941 A | | 12/2009 |
| JP | 2016087479 | * | 5/2016 |
| JP | 2016087479 A | * | 5/2016 |
| JP | 2016087479 A | | 5/2016 |
| JP | 2016148042 A | | 8/2016 |
| JP | 2017100956 A | | 6/2017 |
| WO | 2017015315 A1 | | 1/2017 |

* cited by examiner

METHOD FOR PRODUCING MICROCAPSULES OR BEADS

CROSS-REFERENCE TO RELATED APPLICATIONS

This application is a 371 of PCT/JP2018/029810, filed Aug. 8, 2018, which claims benefit of Japanese Patent Application No. 2017-161323 filed on Aug. 24, 2017.

TECHNICAL FIELD

The present invention relates to a method for producing a microcapsule or microbead containing an encapsulated substance.

BACKGROUND ART

In each of the fields of agriculture, industry, and medical care, microcapsules or microbeads having diameters of several millimeters (mm) to several micrometers (μm) each encapsulating a pesticide, adhesive, ink, heat storage material, pharmaceutical, or the like are used for enabling the improvement of handling, protection of such an encapsulated substance from an external environment, and control of the rate of releasing the encapsulated substance.

As a method for encapsulating a substance (to be encapsulated) in a capsule or the like, an interfacial polymerization method, an in-situ polymerization method, a submerged drying method, and the like are known. In the interfacial polymerization method, particles are formed by using a hydrophobic monomer and a hydrophilic monomer and subjecting them to a polymerization reaction at an oil-water interface. In the in-situ polymerization method, a solution containing a substance to be encapsulated and a monomer serving as a wall material is dispersed in another liquid by stirring to form droplets, and then the monomer is polymerized such that the substance is encapsulated in each capsule (e.g., Patent Literature 1 and 2). In the submerged drying method, a solution in which a substance to be encapsulated has been dispersed or dissolved is dispersed in a medium of water or oil, and then the solvent in which a polymer or the like has been dissolved is removed by heating or depressurization, thereby forming a wall material of the polymer (e.g., Patent Literature 3). However, in the interfacial polymerization method, combinations of monomers are limited. In addition, in the in-situ polymerization method or the submerged drying method, due to the stress load resulting from stirring and the affinity of each substance for other substances, before droplets containing a capsule wall material solidifies such that the capsule wall is formed, a substance to be encapsulated leaks into the liquid other than the droplets. Accordingly, the encapsulation efficiency of the encapsulated substance often remains at a level of less than 40%.

In addition, a spray drying method is known as a method for producing capsules having high encapsulation efficiency. However, in this method, the obtained capsules are limited to those having diameters of several tens of micrometers (μm) or less, and the encapsulation efficiency of a volatile substance is low.

In contrast to these conventional methods, Patent Literature 4 discloses a method for producing microcapsules or microbeads, characterized in that monomer droplets or polymer droplets in which a substance to be encapsulated is dispersed or dissolved are disposed on a water- and oil-repellent flat plate material or a water-repellent flat plate material. Patent Literature 4 provides a method for producing capsules or microbeads with high encapsulation efficiency and high versatility by producing capsules or microbeads in a gas phase.

However, the method disclosed in Patent Literature 4 is problematic in that although the encapsulation efficiency is remarkably improved, the droplets disposed on the flat plate material may roll and coalesce with each other, which may make it difficult to dispose the droplets on the flat plate material at a high density and may cause low production efficiency, and that since the flat plate material on which the droplets are disposed must have liquid repellency so that the droplets do not wet and spread thereon, the degree of freedom as a production method is low.

CITATION LIST

Patent Literature

Patent Literature 1: JP Patent Publication (Kokai) No. 54-49984 A (1979)
Patent Literature 2: JP Patent Publication (Kokai) No. 56-51238 A (1981)
Patent Literature 3: JP Patent Publication (Kokai) No. 2009-292941 A
Patent Literature 4: JP Patent Publication (Kokai) No. 2016-87479 A

SUMMARY OF INVENTION

Technical Problem

As described above, in the conventional methods of producing capsules or microbeads by the in-situ polymerization method or the submerged drying method, the production cost of capsules and the like is high because the encapsulation efficiency of an encapsulated substance is low. In the conventional methods of manufacturing capsules by the spray drying method, the size of capsules that can be produced is limited, and the encapsulation efficiency of a volatile substance is low. Further, in the method of Patent Literature 4 for producing capsules or the like on a liquid-repellent flat plate material, although the encapsulation efficiency is remarkably improved, further improvement in production efficiency and versatility is desired. Therefore, an object of the present invention is to provide a method for producing a capsule or a microbead having high encapsulation efficiency of an encapsulated substance, high production efficiency, and high versatility.

Solution to Problem

The present inventors have studied various means for solving the above problems. As a result, the present inventors found that in the production of capsules or microbeads, the encapsulation efficiency of an encapsulated substance, production efficiency, and versatility can be increased by using monomer droplets or polymer droplets containing the substance to be encapsulated, each of which has a surface coated with a plurality of solid fine particles. This has led to the completion of the present invention.

Specifically, the gist of the present invention is as follows.
(1) A method for producing a microcapsule or microbead, comprising: a step of disposing a monomer droplet or polymer droplet containing a substance to be encapsulated, which has a surface coated with a plurality of solid fine particles, on a flat surface; and a step of solidifying the monomer droplet or polymer droplet disposed on the flat surface in a gas phase so as to form an outer shell of a capsule or microbead, thereby forming a region enclosed by the outer shell, wherein the substance is encapsulated in the region.

(2) The method for producing a microcapsule or microbead according to (1), wherein there are a plurality of regions enclosed by the outer shell, and the substance is encapsulated in each of the regions.

(3) The method for producing a microcapsule or microbead according to (1) or (2), further comprising a step of removing the solid fine particles from the microcapsule or microbead.

(4) The method for producing a microcapsule or microbead according to any one of (1) to (3), wherein the step of solidifying the monomer droplet disposed on the flat surface in a gas phase comprises polymerizing the monomer droplet on the flat surface, and the step of solidifying the polymer droplet disposed on the flat surface in a gas phase comprises removing a solvent in the polymer droplet.

(5) The method for producing a microcapsule or microbead according to (4), wherein the monomer is at least one selected from a (meth)acrylate, a styrene-based monomer, and divinylbenzene.

(6) A microcapsule or microbead, comprising an outer shell which is made of a polymer and a substance which is encapsulated in a region enclosed by the outer shell.

(7) The microcapsule or microbead according to (6), wherein there are a plurality of regions enclosed by the outer shell, and the substance is encapsulated in each of the regions.

(8) The microcapsule or microbead according to (6), wherein the outer shell has a substantially uniform thickness.

(9) The microcapsule or microbead according to (6), wherein the polymer is a polymer formed from at least one monomer selected from a (meth)acrylate, a styrene-based monomer, and divinylbenzene.

(10) The microcapsule or microbead according to any one of (6) to (9), wherein there are no fine particles adhering to the surface of the outer shell.

(11) The microcapsule or microbead according to any one of (6) to (9), wherein traces of removing fine particles remain on the surface of the outer shell.

The present description includes part or all of the contents as disclosed in the description and/or drawings of Japanese Patent Application No. 2017-161323, which is a priority document of the present application.

Advantageous Effects of Invention

According to the present invention, a method for producing a capsule or a microbead having high encapsulation efficiency of an encapsulated substance, high production efficiency, and high versatility is provided.

DESCRIPTION OF EMBODIMENTS

Figure 1:
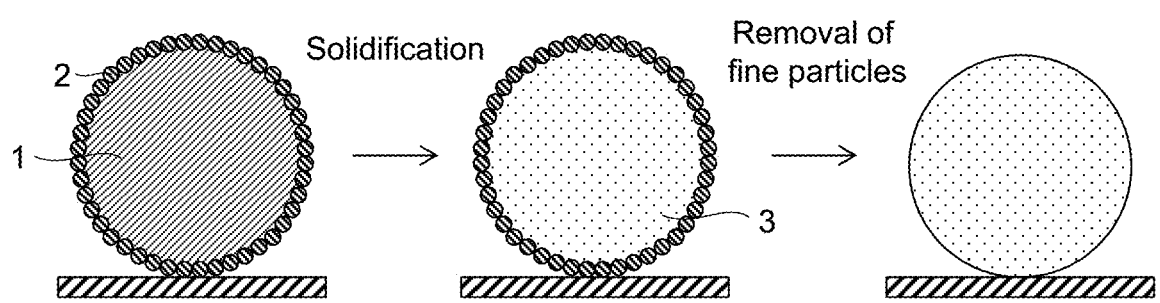
FIG. 1 is a process chart depicting one embodiment of the method of the present invention.

Hereinafter, preferred embodiments of the present invention will be described in detail.

The present invention relates to a method for producing a microcapsule or microbead. The microcapsule or microbead of the present invention comprises an outer shell made of a polymer which is formed from a monomer droplet or polymer droplet of a wall material and a substance encapsulated in a region enclosed by the outer shell. In the present invention, the term "capsule" refers to a capsule in which a single hole or a plurality of holes are present. In the present invention, the term "microbead" refers to a microbead which has no pore therein and is completely filled with a matrix.

The shape of the microcapsule or microbead of the present invention is not particularly limited, and may be, for example, spherical, pseudo-spherical, or flat, but preferably spherical from the viewpoint of higher capsule or microbead strength. The microcapsule or microbead of the present invention has a particle size of, for example, several micrometers (μm) to several centimeters (cm), which is preferably 100 μm to 5 mm. The microcapsule or microbead of the present invention may be either a mononuclear type in which the encapsulated substance forms one nucleus in the capsule, or a multinuclear type in which the encapsulated substance forms a plurality of nuclei in the capsule. In the case of the multinuclear type, there are a plurality of regions enclosed by the outer shell, and each region comprises the encapsulated substance. The method of the present invention is excellent in that all capsules can be made mononuclear and the thickness of an outer shell (hereinafter also referred to as "capsule wall") can be made substantially uniform, which are extremely difficult with the conventional methods, particularly in producing mononuclear (hollow) capsules.

The present invention is characterized by disposing monomer droplets or polymer droplets containing a substance to be encapsulated, each of which has a surface coated with a plurality of solid fine particles. More specifically, the method of the present invention comprises: a step of disposing a monomer droplet or polymer droplet containing a substance to be encapsulated, which has a surface coated with a plurality of solid fine particles, on a flat surface (step 1); and a step of obtaining a microcapsule or microbead by solidifying the monomer droplet or polymer droplet disposed on the flat surface in a gas phase so as to form an outer shell of a capsule or microbead, thereby forming a region enclosed by the outer shell (step 2). The method of the present invention may further comprise a step of removing the solid fine particles from the microcapsule or microbead (step 3) after step 2.

In the method of the present invention, formation of capsules or microbeads by forming and solidifying droplets is performed in a gas phase (in the air). Therefore, leakage of a substance to be encapsulated can be prevented, and the substance can be encapsulated in capsules or microbeads with high encapsulation efficiency. Further, according to the method of the present invention, as a result of coating the surface of each of monomer droplets or polymer droplets with a plurality of solid fine particles, the droplets are unlikely to roll and do not coalesce with each other when they are in light contact, making it possible to dispose the droplets at a high density. Therefore, production efficiency is improved, and the droplets are stabilized so as not to wet and spread even on a non-liquid-repellent flat surface, and thus, the nature of the flat surface on which the droplets are disposed is not limited, and the production method has a high degree of freedom.

According to the method of the present invention, the particle size of capsules or microbeads obtained can be adjusted by adjusting the size of droplets disposed on a flat surface. For example, capsules or microbeads having a particle size of 1.5 mm to 3 mm can be obtained from 2 μL to 10 μL of droplets. The particle size of capsules or microbeads can be measured by a stereoscopic microscope or a laser diffraction scattering method.

FIG. 1 is a process chart depicting one embodiment of the method of the present invention. FIG. 1 is a cross-sectional view of a microcapsule or microbead in a direction perpendicular to the flat surface. As illustrated in FIG. 1, according to the production method of the present invention, a monomer droplet or polymer droplet 1 containing a substance to be encapsulated, which has a surface coated with a plurality of solid fine particles 2, is disposed on a flat surface (left diagram in FIG. 1) in step 1. The monomer droplet or polymer droplet disposed on a flat surface is in a so-called liquid marble form in which the surface of a monomer droplet or polymer droplet 1 containing a substance to be encapsulated is covered with a plurality of solid fine particles 2. In step 2, a microcapsule or microbead 3 which has a surface coated with a plurality of solid fine particles 2 is obtained by solidifying the monomer droplet or polymer droplet disposed on the flat surface in a gas phase so as to form an outer shell of a capsule or microbead, thereby forming a region enclosed by the outer shell (center diagram in FIG. 1). In the microcapsule or microbead 3, the substance is encapsulated in a region enclosed by an outer shell made of a polymer which is formed from a monomer droplet or polymer droplet. In the optional step 3, the solid fine particles 2 are removed from the microcapsule or microbead 3 coated with the solid fine particles 2 (right diagram in FIG. 1). Hereinafter, each of steps 1 to 3 will be described in detail.

In step 1, monomer droplets or polymer droplets containing a substance to be encapsulated, each of which has a surface coated with a plurality of solid fine particles, are prepared, and the droplets are disposed on a flat surface.

A substance to be encapsulated can be selected according to the purpose of the capsule or microbead. A substance to be encapsulated is not particularly limited, and either an oil-soluble substance or a water-soluble substance can be used. Substances to be encapsulated may be used alone or in combination of two or more thereof.

Examples of an oil-soluble substance to be encapsulated include, but are not particularly limited to, oil-soluble pesticides, adhesives, inks, heat storage materials, and pharmaceuticals. For example, a cooling medium such as tetradecane, a fat-soluble vitamin such as α-tocopherol, an antioxidant, and an anticancer agent such as doxorubicin can be used.

Examples of a water-soluble substance to be encapsulated include, but are not particularly limited to, water-soluble pesticides, adhesives, inks, heat storage materials, and pharmaceuticals. For example, solvents such as water and proteins such as bovine serum albumin can be used.

A substance to be encapsulated may be volatile or non-volatile. According to the production method of the present invention, both volatile and non-volatile substances can be encapsulated in capsules or microbeads with high encapsulation efficiency. The method is excellent in that in particular, in the spray drying method, a volatile substance having low encapsulation efficiency can be encapsulated at high encapsulation efficiency.

A substance to be encapsulated is preferably in a liquid form, and it can be directly used. It is also possible to dissolve or disperse a substance to be encapsulated in a liquid or solid form in a solvent for using the substance. The solvent can be appropriately selected according to the substance to be encapsulated which is used herein. When the substance to be encapsulated is oil-soluble, for example, organic solvents such as acetone, methanol, ethanol, dimethyl sulfoxide, dichloroethane, dichloromethane, hexane, xylene, ethyl acetate, chloroform, and diethyl ether can be used. When the substance to be encapsulated is water-soluble, for example, solvents such as water can be used.

According to the present invention, when monomer droplets are used, either a hydrophobic monomer or a hydrophilic monomer can be used as a monomer.

In the present invention, the term "hydrophobic monomer" refers to a monomer having a solubility in water at 25° C. of less than 2% by weight. Examples of a hydrophobic monomer include, but are not particularly limited to: monofunctional acrylates such as isopropyl acrylate, n-butyl acrylate, isobutyl acrylate, n-amyl acrylate, isoamyl acrylate, n-hexyl acrylate, 2-ethylhexyl acrylate, n-octyl acrylate, decyl acrylate, and dodecyl acrylate; polyfunctional acrylates such as ethylene glycol diacrylate, polyethylene glycol diacrylate, trimethylolpropane triacrylate, and pentaerythritol tetraacrylate; monofunctional methacrylates such as ethyl methacrylate, propyl methacrylate, n-butyl methacrylate, isobutyl methacrylate, n-amyl methacrylate, n-hexyl methacrylate, 2-ethylhexyl methacrylate, n-octyl methacrylate, and decyl methacrylate; polyfunctional methacrylates such as ethylene glycol dimethacrylate, polyethylene glycol dimethacrylate, trimethylolpropane trimethacrylate, and pentaerythritol tetramethacrylate; styrene monomers such as styrene, α-methylstyrene, vinyltoluene, t-butylstyrene, and chloromethylstyrene; and divinylbenzene. Hydrophobic monomers may be used alone or in combination of two or more thereof. Preferable hydrophobic monomers are (meth)acrylate, styrene, and divinylbenzene from the viewpoint of the mechanical strength of the wall of the capsule or microbead. In the present invention, the term "(meth)acrylate" refers to a monofunctional or polyfunctional acrylate and/or methacrylate.

In the present invention, the term "hydrophilic monomer" refers to a monomer having a solubility in water at 25° C. of 2% by weight or more. Examples of a hydrophilic monomer include, but are not particularly limited to, acrylic acid, methacrylic acid, maleic acid, fumaric acid, vinyl sulfonic acid, styrene sulfonic acid, vinyl alcohol, acrylamide, and methacryloxyethyl phosphate. Hydrophilic monomers may be used alone or in combination of two or more thereof.

The monomer droplets may include other components different from the monomer components and the substance to be encapsulated. Examples of other components include, but are not particularly limited to, a solvent for dissolving or dispersing a monomer, a polymerization initiator such as a thermal polymerization initiator or a photopolymerization initiator, a surfactant, a UV absorber, a light stabilizer, an antioxidant, a flame retardant, a plasticizer, and a wax.

Examples of a thermal polymerization initiator include, but are not limited to: azo compounds such as 2,2'-azobis (4-methoxy-2,4-dimethylvaleronitrile), 2,2'-azobis(2,4-dimethylvaleronitrile), dimethyl-2,2'-azobis(2-methylpropionate), 2,2'-azobis(2-methylbutyronitrile), 1,1'-azobis(cyclohexane-1-carbonitrile), 2,2'-azobis[N-2-propenyl)2-methylpropionamide], 1-[(1-cyano-1-methylethyl)azo]formamide, 2,2'-azobis(N-butyl-2-methylpropionamide), and 2,2'-azobis(N-cyclohexyl-2-methylpropionamide); and peroxides such as t-butylperoxybenzoate and 2,5-dimethyl-2,5-di(t-butylperoxy)hexane. Of these, azo compounds are preferable, and 2,2'-azobis(4-methoxy-2,4-dimethylvaleronitrile) is more preferable. The blending amount of a thermal polymerization initiator is preferably in a range of 0.01 mol % to 5 mol % based on the monomer.

Examples of a photopolymerization initiator include, but are not particularly limited to: acetophenone-based compounds such as diethoxyacetophenone; benzoin-based compounds such as benzoin, benzoin methyl ether, and benzoin isopropyl ether; acylphosphine oxide compounds such as 2,4,6-trimethylbenzoindiphenylphosphine oxide; benzophenone-based compounds such as benzophenone and hydroxybenzophenone; thioxanthone-based compounds such as 2-isopropylthioxanthone and 2,4-dimethylthioxanthone; aminobenzophenone-based compounds such as 4,4'-diethylaminobenzophenone; and 10-butyl-2-chloroacridone, 2-ethylanthraquinone, 9,10-phenanthrenequinone, and camphorquinone. The blending amount of a photopolymerization initiator is preferably in a range of 0.01 mol % to 5 mol % based on the monomer.

In order to carry out a curing reaction of a monomer more efficiently, a photopolymerization initiator can be used in monomer droplets in combination with a photopolymerization accelerator, if necessary. Examples of a photopolymerization accelerator include, but are not particularly limited to: benzoic acid compounds such as 4-dimethylaminobenzoic acid, ethyl 4-dimethylaminobenzoate, n-butoxyethyl 4-dimethylaminobenzoate, isoamyl 4-dimethylaminobenzoate, and 2-ethylhexyl 4-dimethylaminobenzoate; and tertiary amine compounds such as triethanolamine, methyldiethanolamine, triisopropanolamine, 4,4'-dimethylaminobenzophenone, and 4,4'-diethylaminobenzophenone. The blending amount of a photopolymerization accelerator is preferably in a range of 0.01 mol % to 5 mol % based on the monomer.

According to the present invention, when polymer droplets are used, a polymer is not particularly limited, and a polymer derived from a monomer that can be used in the present invention can be used. For example, polymers derived from the above-described hydrophobic or hydrophilic monomers, and preferably poly(meth)acrylate, polystyrene, and polydivinylbenzene can be used. Further, polylactic acid, polyglycolic acid, a copolymer of lactic acid and glycolic acid, polycaprolactone, and the like can also be used. The polymer is usually dissolved in a solvent such as an organic solvent and used in the form of a polymer solution. An organic solvent is selected according to the polymer used. Examples thereof include acetone, methanol, ethanol, dimethylsulfoxide, dichloroethane, dichloromethane, hexane, toluene, xylene, ethyl acetate, chloroform, and diethyl ether.

The polymer droplets may include other components different from the polymer components, the solvent, and the substance to be encapsulated. Examples of other components include, but are not particularly limited to, a surfactant, a UV absorber, a light stabilizer, an antioxidant, a flame retardant, a plasticizer, and a wax.

Solid fine particles covering the surface of a monomer droplet or a polymer droplet are used for stably disposing the droplet on a flat surface. Therefore, the capsule or microbead obtained by the method of the present invention does not have a capsule or microbead wall formed with solid fine particles. Solid particulates have a smaller particle size than the monomer droplet or polymer droplet. The particle size of solid fine particles is not particularly limited as long as it is small enough to cover a monomer droplet or a polymer droplet, but is preferably 0.01 µm to 500 µm, and more preferably 1 µm to 300 µm. According to the present invention, the particle size of solid fine particles means the number-based average particle size measured by a stereoscopic microscope or a laser diffraction scattering method. When the particle size of solid fine particles is in this range, the entire or almost entire monomer droplet or polymer droplet can be covered, and coalescence of such droplets can be avoided. Thus, the droplets can be disposed at a high density, thereby increasing production efficiency. Note that monomer droplets or polymer droplets only need to be disposed on a flat surface without wetting and spreading, and thus, they may be in a form in which each droplet is partially coated with solid fine particles. When the particle size (diameter) of monomer droplets or polymer droplets is, for example, about 1 mm to 3 mm, the particle size of solid fine particles is, for example, 1 µm to 300 µm.

Solid fine particles preferably have appropriate wettability with respect to monomer droplets or polymer droplets in order to stably cover the droplets. Solid particles are preferably liquid-repellent, i.e., water- and oil-repellent, or water-repellent. In the present invention, the term "water- and oil-repellent" means having water repellency and oil repellency. Solid fine particles only need to have at least appropriate wettability with respect to droplets on the surface of each fine particle, and preferably have water/oil repellency or water repellency.

Water-repellent solid fine particles are not particularly limited, and have a contact angle with water of, for example, 70° or more and preferably 100° or more. Examples of water-repellent solid fine particles include fine particles of Teflon (registered trademark), alkylated silica particles, carbon black, polyvinylidene fluoride, and poly(2-(perfluorooctyl)ethyl acrylate).

In addition to the above water-repellent solid fine particles, for example, an aerogel or xerogel silicone monolith having a polysiloxane structure can be used instead of water-repellent solid fine particles. This silicone monolith can be obtained by, for example, using both a bifunctional alkoxysilane and a trifunctional alkoxysilane or a tetrafunctional or higher alkoxysilane as starting materials and copolymerizing these silanes by a sol-gel reaction. Examples of such a silicone monolith include an aerogel or xerogel silicone monolith which is obtained from vinyltrimethoxysilane and methylvinyldimethoxysilane and has a structure represented by the following formula (1):

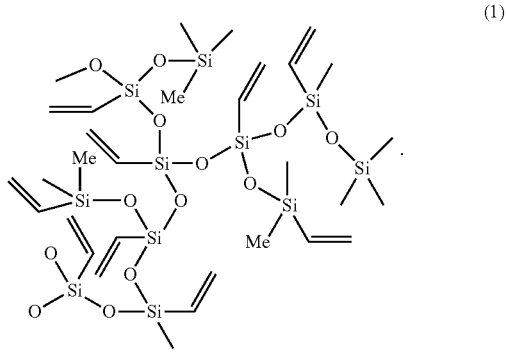 [SMILES: C=C[Si](C)(C)O[Si](C=C)(O[Si](C)(C=C)O[Si](C)(C)C)O[Si](C=C)(O[Si](C=C)(OC)O[Si](C)(C)C)O[Si](C=C)(O[Si](C)(C)C=C)O[Si](C)(C=C)O[Si](O)(O)C=C]

Such material is described in the report of Hayase et al. (Angew Chem Int Ed Engl.2013, 52 (41), 10788-10791). Water-repellent solid fine particles may have oil repellency as well as water repellency.

Water- and oil-repellent solid fine particles are not particularly limited, and have a contact angle with water of, for example, 70° or more, preferably 100° or more, and a contact angle with n-hexadecane of, for example, 70° or more, preferably 100° or more. Water- and oil-repellent solid fine particles preferably have a contact angle with water of 150° or more and a contact angle with n-hexadecane of 140° or more.

Water- and oil-repellent solid fine particles are not particularly limited. For example, a material having a polysiloxane structure and a perfluoroalkyl structure, preferably an aerogel or xerogel silicone monolith having a polysiloxane structure and a perfluoroalkyl structure can be used. The silicone monolith is obtained by, for example, adding an alkyl fluoride chain to a vinyl group of the silicone monolith having the structure of the above formula (1). The addition of an alkyl fluoride chain can be carried out by, for example, reacting the silicone monolith having the structure of the above formula (1) with alkylthiol by a thiol-ene click reaction. Marshmallow gel described in the report of Hayase et al. (Angew Chem Int Ed Engl.2013, 52 (41), 10788-10791), which is a flexible porous material exhibiting water and oil repellency, can be used as such material.

In addition to the water- and oil-repellent solid fine particles described above, for example, fine particles of carbon surface-modified with a perfluoroalkyl group, polyvinylidene fluoride, or the like can be used as water- and oil-repellent solid fine particles.

As a combination of a monomer or polymer and solid fine particles, in order to stably cover droplets of a monomer or polymer with solid fine particles, it is preferable that the monomer or polymer is hydrophobic and the solid fine particles are water- and oil-repellent, or the monomer or polymer is hydrophilic and the solid fine particles are water- and oil-repellent or water-repellent.

In the preparation of a monomer droplet or polymer droplet containing a substance to be encapsulated which has a surface coated with a plurality of solid fine particles, the timing of adding the substance to be encapsulated to the monomer droplet or polymer droplet may be either before or after coating the droplet with the solid fine particles. In other words, it is possible to obtain a monomer droplet or polymer droplet containing a substance to be encapsulated and then coating the droplet with solid fine particles, or it is also possible to coating a monomer droplet or polymer droplet lacking a substance to be encapsulated with solid fine particles and then adding a substance to be encapsulated to the droplet. When coating a monomer droplet or polymer droplet containing a substance to be encapsulated with solid fine particles, a monomer droplet or polymer droplet containing a substance to be encapsulated can be obtained by preparing a monomer or polymer solution or suspension in which a substance to be encapsulated is dissolved or dispersed by, for example, mixing a substance to be encapsulated and a monomer or polymer solution and dropping the solution or suspension. When adding a substance to be encapsulated to a monomer droplet or polymer droplet coated with solid fine particles, the substance may be added in such a way that the shape of the droplet is not destroyed. For example, the substance can be added by injecting a substance to be encapsulated in a liquid form or a solution of a substance to be encapsulated into the droplet using a syringe needle or the like.

According to the present invention, the monomer droplet or polymer droplet containing a substance to be encapsulated may be in a form in which the substance to be encapsulated is present in the monomer droplet or polymer droplet, and the form is not particularly limited. It may be in a form in which the substance to be encapsulated is dissolved or dispersed in the droplet or in a form in which the substance to be encapsulated is present in a mononuclear state in the droplet.

According to the present invention, the content of the substance encapsulated in each monomer droplet or polymer droplet is not particularly limited, and is, for example, 0.01% to 90% by weight, preferably 1% to 80% by weight with respect to the weight of the monomer or polymer.

Coating of the monomer or polymer droplet surface with a plurality of solid fine particles is not particularly limited. For example, coating can be performed by preparing droplets by dropping a solution or suspension of a monomer or polymer and, for example, sprinkling a powder of solid fine particles on the surface of each droplet, embedding the droplets in a powder of solid fine particles, or rolling the droplets on a powder of solid fine particles, thereby treating the droplets with the solid fine particles. The solution or suspension of the monomer or polymer to be dropped may or may not comprise a substance to be encapsulated as described above.

Each monomer or polymer droplet is disposed on a flat surface. A material having a flat surface on which monomer or polymer droplets are disposed is not particularly limited in terms of shape and material thereof as long as it has a flat portion so that the droplets can be disposed thereon stably. For example, a container such as a glass petri dish or a beaker, or a flat plate material of any material can be used. According the present invention, by covering the surface of each monomer droplet or polymer droplet with a plurality of solid fine particles, the droplet can be stably disposed regardless of the properties of the flat surface.

In step 2 of the present invention, a monomer droplet or polymer droplet disposed on a flat surface is solidified in a gas phase (in the air) so as to form an outer shell of a capsule or microbead, thereby forming a region enclosed by the outer shell. Thus, a microcapsule or microbead in which a substance to be encapsulated is encapsulated in a region enclosed by the outer shell is obtained. The outer shell of the capsule or microbead consists of a polymer formed from a monomer droplet or polymer droplet of a wall material. According to the present invention, by solidifying the monomer droplet or polymer droplet in the gas phase, it is possible to prevent the substance to be encapsulated from leaking, and to increase encapsulation efficiency of the encapsulated substance. The microcapsule or microbead obtained in step 2 is in a form in which it is coated with solid fine particles. The microcapsule or microbead may be used in a form in which it is coated with solid fine particles, but preferably used after removing the solid fine particles by the following step 3.

According to the method of the present invention, when a monomer droplet is used, preferably, the monomer droplet containing a substance to be encapsulated is polymerized (cured) on a flat surface in a gas phase to solidify the droplet, thereby obtaining a capsule or microbead in which the substance is encapsulated in a region enclosed by an outer shell made of a polymer formed from the monomer.

The polymerization of monomer droplets can be carried out by a usual monomer polymerization method, but thermal polymerization and photopolymerization are preferable. When the substance to be encapsulated is a volatile substance or a water-soluble substance, photopolymerization is preferable because encapsulating efficiency is improved.

The reaction conditions for thermal polymerization are appropriately selected depending on the type of the monomer and the substance to be used. For example, the reaction temperature is 30° C. to 80° C., and the reaction time is 0.5 to 20 hours.

The reaction conditions for photopolymerization are appropriately selected depending on the type of the monomer and the substance to be encapsulated which are used herein. For example, under irradiation of visible light of 380 to 780 nm, preferably 430 to 485 nm, the reaction temperature is 0° C. to 50° C., preferably a temperature around room temperature (20° C. to 25° C.), and the reaction time is 0.02 to 60 minutes.

According to the method of the present invention, when a polymer droplet is used, the polymer droplet disposed on a flat surface is solidified by, for example, drying such that a capsule or microbead in which a substance to be encapsulated is encapsulated in a region enclosed by an outer shell made of the polymer can be obtained. The drying of polymer droplets can be performed by, for example, removing the solvent in the polymer droplets by evaporation or the like. The drying of polymer droplets is not particularly limited as long as the solvent in the polymer droplets can be removed by evaporation or the like. For example, the drying is carried out under reduced pressure conditions of 1 to 101324 Pa. The drying of polymer droplets may be performed at room temperature (25° C.) in the air. Further, polymer droplets may be frozen before drying the polymer droplets. The drying of polymer droplets can also be carried out by treating the polymer droplets by shaking, preferably horizontal shaking (rotary shaking).

Step 3 of the present invention is an optional step that can be performed subsequent to step 2. In the method of the present invention, step 3 is preferably performed after step 2. In step 3, solid fine particles are removed from the microcapsules or microbeads coated with the solid fine particles obtained in step 2. The removal of the solid fine particles can be performed by, for example, wiping off with a cloth such as a paper waste cloth or blowing a high-pressure gas. When step 3 is performed, there are no fine particles adhering to the surface of the outer shell of each obtained microcapsule or microbead. When step 3 is performed, traces of removing fine particles may remain on the surface of the outer shell of each obtained microcapsule or microbead. The adhesion of fine particles and the traces of removing fine particles can be confirmed by, for example, microscopically observing the microcapsules or microbeads.

In one embodiment of the present invention, mononuclear spherical microcapsules can be produced. According to the method of the present invention, all capsules can be made mononuclear and the thickness of a capsule wall corresponding to an outer shell can be made substantially uniform, which is extremely difficult with the conventional methods. Therefore, the present invention also relates to a method for producing a mononuclear spherical microcapsule.

In this embodiment, the method for producing a mononuclear (hollow) spherical microcapsule of the present invention may comprise steps 1 and 2 described above, i.e., a step of disposing a monomer droplet or polymer droplet containing a substance to be encapsulated, which has a surface coated with a plurality of solid fine particles, on a flat surface (step 1) and a step of obtaining a microcapsule or microbead by solidifying the monomer droplet or polymer droplet disposed on the flat surface in a gas phase so as to form an outer shell of a capsule or microbead, thereby forming a region enclosed by the outer shell (step 2), and may further comprise a step of removing the solid fine particles from the microcapsule or microbead (step 3). Details of each step are the same as described above. In this embodiment, it is preferable to use monomer droplets.

In this embodiment, in the preparation of the monomer droplet or polymer droplet containing a substance to be encapsulated which has a surface coated with a plurality of solid fine particles in step 1, the timing of adding the substance to be encapsulated to the monomer droplet or polymer droplet may be either before or after coating the droplet with the solid fine particles. The addition of the substance to be encapsulated to the monomer droplet or polymer droplet is preferably performed in such a manner that the substance is not dissolved in the droplet in order to obtain a mononuclear capsule. For example, it can be carried out by injecting the substance into the droplet using a syringe needle.

In this embodiment, it is preferable that the substance to be encapsulated is not dissolved in the monomer droplet or polymer droplet in order to make a capsule mononuclear. Examples of a combination of a substance to be encapsulated and a monomer used as above include a combination of an oil-soluble substance to be encapsulated and a hydrophilic monomer, a water-soluble substance to be encapsulated such as water or an aqueous solution and a hydrophobic monomer such as a (meth)acrylate. Examples of a combination of a substance to be encapsulated and a polymer used as above include a combination of an oil-soluble substance to be encapsulated and a hydrophilic polymer, and a combination of a water-soluble substance to be encapsulated and a hydrophobic polymer.

In this embodiment, in step 2 of solidifying the monomer droplet or polymer droplet in the gas phase, it is preferable that the droplet is treated by shaking, preferably horizontal shaking (rotary shaking). Thus, a capsule having a high degree of sphericity and a high degree of uniformity of the thickness of the capsule wall can be obtained. A capsule having a high degree of sphericity and a high degree of uniformity of the thickness of the capsule wall is preferable in that an inevitable decrease in capsule strength when the volume of the hollow portion is increased can be minimized. In this step, by adjusting the shaking speed and the shaking time until the start of solidification, it is possible to obtain a capsule in which the degree of sphericity and the degree of uniformity of the thickness of the capsule wall are optimized. Specifically, when shaking treatment is performed by horizontal shaking treatment (rotary shaking), the shaking speed is 120 to 140 rpm, preferably about 130 rpm, and the shaking time until the start of solidification is 0 second (i.e., solidification is started at the same time as the start of shaking). Accordingly, a mononuclear spherical capsule having a higher degree of sphericity, a more spherical shape, and a substantially uniform capsule wall thickness can be obtained. In a preferred embodiment, the monomer droplet is solidified by photopolymerization at a shaking speed of about 130 rpm for a shaking time of 0 second until the start of photopolymerization in the above case.

The present invention also includes microcapsules or microbeads obtained by the above-described production method.

The microcapsule or microbead of the present invention comprises an outer shell made of a polymer and a substance encapsulated in a region enclosed by the outer shell (hollow region). In the present invention, the outer shell is formed by solidifying a monomer droplet or polymer droplet in a gas phase. When a monomer droplet is used, a polymer constituting the outer shell is preferably formed by polymerizing the monomer droplet. Therefore, the polymer constituting the outer shell is a polymer formed by polymerizing the monomer described above for the monomer droplet, or the polymer described above for the polymer droplet. Preferably, the polymer constituting the outer shell is a polymer formed from at least one monomer selected from a (meth) acrylate, a styrene-based monomer, and divinylbenzene. The substance to be encapsulated that can be used for the microcapsule or microbead of the present invention is as described above for the production method.

The microcapsule or microbead may be either a mononuclear type in which the encapsulated substance forms one nucleus in the capsule, or a multinuclear type in which the encapsulated substance forms a plurality of nuclei in the capsule. In the case of the multinuclear type, there are a plurality of regions enclosed by the outer shell, and each region comprises the encapsulated substance.

In one embodiment, the microcapsule or microbead is of the mononuclear type. In a preferred embodiment, the microcapsule or microbead is of the mononuclear type, and the thickness of the outer shell thereof is substantially uniform. The microcapsule or microbead has an average coefficient of variation of preferably less than 0.4, preferably less than 0.3, and more preferably less than 0.2 in the evaluation of the degree of uniformity of the outer shell (capsule wall) described in the Examples below.

Preferably, there are no fine particles adhering to the surface of the outer shell of the microcapsule or microbead. In addition, traces of removing fine particles may remain on the surface of the outer shell of the microcapsule or microbead. The traces of removing fine particles are traces which remain when solid fine particles present on the surface of the outer shell are wiped off with a cloth such as a paper waste cloth or are removed by blowing a high-pressure gas in step 3 of the method for producing a microcapsule or microbead. The adhesion of fine particles and the traces of removing fine particles on microcapsules or microbeads can be confirmed by, for example, microscopically observing microcapsules or microbeads.

EXAMPLES

Hereinafter, the present invention will be described more specifically with reference to the Examples. However, the technical scope of the present invention is not limited to these Examples.
(Preparation of Solid Fine Particles)

According to the report of Hayase et al. (Angew Chem Int Ed Engl.2013, 52 (41), 10788-10791), marshmallow gel, which is a flexible porous material exhibiting water and oil repellency, was prepared for solid fine particles.

Specifically, 0.8 g of n-hexadecyltrimethylammonium chloride and 5 g of urea were added to 15 mL of a 5 mM aqueous acetic acid solution in a glass container, followed by mixing. Next, 0.0210 mol of vinyltrimethoxysilane and 0.0140 mol of methylvinyldimethoxysilane were added, and the mixture was stirred with a stirrer for 30 minutes. Thereafter, the resulting solution was transferred to a sealed container, gelled at 80° C., and aged for 2 days under basic conditions by hydrolysis of urea. The obtained wet gel was impregnated with a water/isopropyl alcohol (1:1) solution, washed with isopropyl alcohol, and dried.

Next, an alkyl fluoride chain was added to the vinyl group of the obtained gel by a thiol-ene click reaction. Specifically, 0.5 g of the above gel was immersed in 50 ml of a 2-propanol solution containing 10% (v/v) 1H,1H,2H,2H-perfluorodecanethiol and 0.1% (w/v) 2,2'-azobis(isobutyronitrile) (AIBN) and reacted at 60° C. for 10 hours. The obtained gel was washed with 2-propanol and dried, thereby obtaining solid marshmallow gel. The contact angle of the obtained marshmallow gel with water was 160°, and the contact angle thereof with n-hexadecane was 151°.

The obtained marshmallow gel was ground using a mortar, thereby obtaining a fine particle powder having a particle size (diameter) of 100 μm or less. The particle size of the marshmallow gel fine particles was measured by a stereoscopic microscope.

Example 1

Tetradecane was used as a substance to be encapsulated, and trimethylolpropane trimethacrylate was used as a wall material monomer. Camphorquinone (1 mol %) serving as a photopolymerization initiator and ethyl 4-(dimethylamino) benzoate (1 mol %) serving as a polymerization accelerator were dissolved in trimethylolpropane trimethacrylate. Subsequently, tetradecane was added to the obtained solution such that the weight ratio of trimethylolpropane trimethacrylate:tetradecane was 4:6. Droplets (5 μL) of the obtained solution were added dropwise onto the marshmallow gel fine particle powder, rolled on the powder such that the marshmallow gel fine particle powder was sprinkled on the droplets, thereby preparing monomer droplets which were entirely coated with the marshmallow gel fine particles (liquid marbles). The liquid marbles were disposed on a glass petri dish. The liquid marbles were stable and did not wet and spread thereon. In addition, they could be disposed at a high density without coalescing with each other even when a plurality thereof were disposed on a flat surface. The liquid marbles were irradiated with visible light having a wavelength of 430 to 485 nm and an intensity of 1200 mW/cm$^2$ or more per liquid marble at 20° C. for 2 minutes to perform photopolymerization of the monomer, thereby solidifying the monomer droplets. Thus, spherical solid microbeads in which tetradecane was encapsulated in a polymer formed from trimethylolpropane trimethacrylate were obtained. The marshmallow gel fine particles on the microbead surface were removed by wiping off with Kimwipes (manufactured by NIPPON PAPER CRECIA CO., LTD.). The encapsulation efficiency of tetradecane in the obtained microbeads (=the amount encapsulated in the capsules/the amount prepared×100) was 100±3%, indicating that encapsulation can be achieved with high efficiency. The particle size of the microbeads was 2 mm.

The surface characteristics of the microbeads obtained in Example 1 were evaluated. Each microbead was immersed in water before and after removing the marshmallow gel fine particles on the microbead surface. The microbead coated with the marshmallow gel fine particles did not sink in water and showed water repellency, but the microbead from which the marshmallow gel fine particles were removed sank in water and showed no water repellency.

Figure 2:
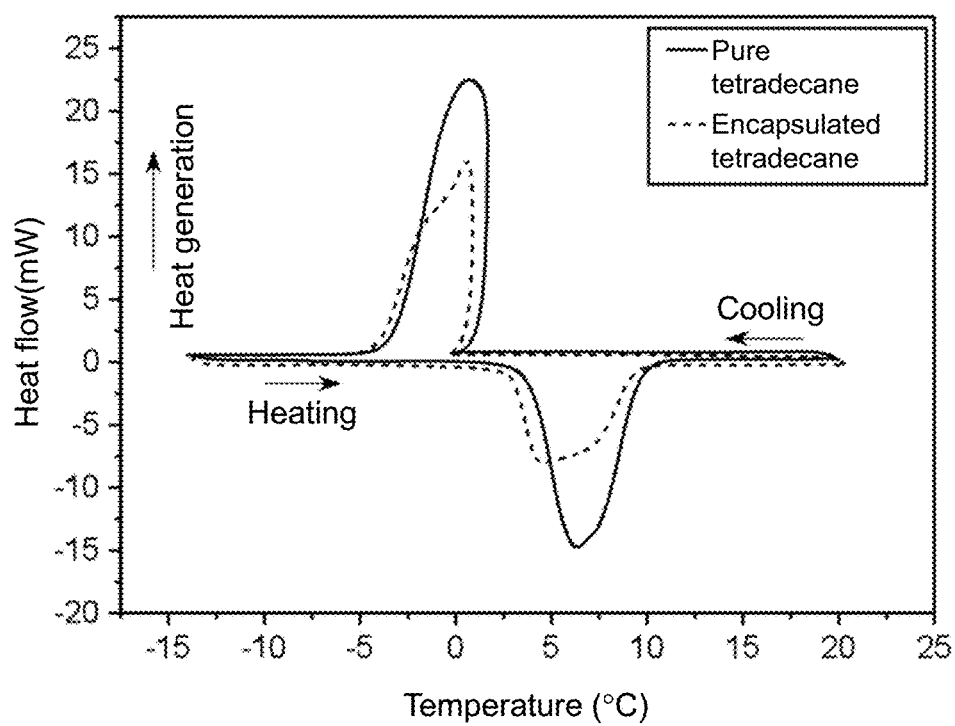
FIG. 2 is a diagram depicting the results of DSC measurement of pure tetradecane and tetradecane in the microbeads obtained in Example 1.

The heat characteristics of tetradecane (encapsulated tetradecane) in the microbeads obtained in Example 1 were evaluated by differential scanning calorimetry (DSC) (DSC-60, manufactured by Shimadzu Corporation). As a comparison, the heat characteristics of pure tetradecane which was not encapsulated in the microbeads were determined. The results are shown in Table 1 and FIG. 2. FIG. 2 is a diagram depicting the results of DSC measurement of pure tetradecane and tetradecane in the microbeads obtained in Example 1.

TABLE 1

|  | Melting point (° C.) | Solidifying point (° C.) | Phase transition enthalpy (J/g-tetradecane) | |
|---|---|---|---|---|
|  |  |  | Heating | Cooling |
| Pure tetradecane | 6.5 | 0.8 | 222 | 225 |
| Encapsulated tetradecane | 4.8 | 0.7 | 228 | 226 |

Table 1 and FIG. 2 showed that the tetradecane in the microbeads of Example 1 retained the heat characteristics unique to tetradecane.

Example 2

Figure 3:
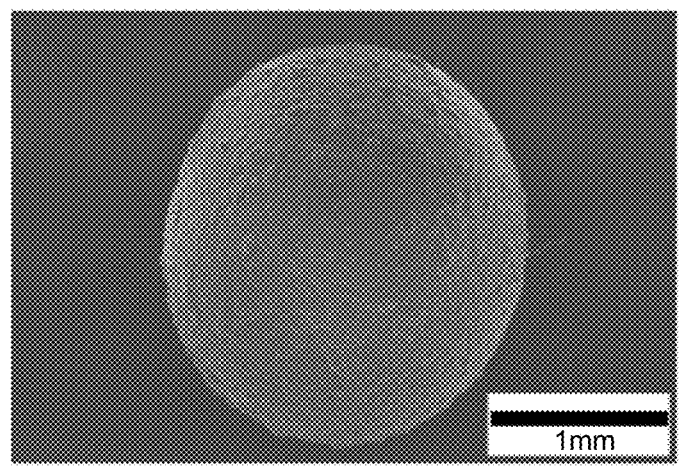
FIG. 3 is a microscopic photograph of a microbead obtained in Example 2.

Spherical solid microbeads encapsulating α-tocopherol were obtained in the same manner as in Example 1 except that the encapsulated substance, tetradecane, was replaced with α-tocopherol, the weight ratio of trimethylolpropane trimethacrylate:α-tocopherol was 9:1, and the visible light irradiation time was changed to 4 minutes. FIG. 3 is a microscopic photograph of a microbead obtained in Example 2. The encapsulation efficiency of α-tocopherol in the obtained microbeads was 103±3%, and the particle size was 2 mm.

Example 3

Figure 4:
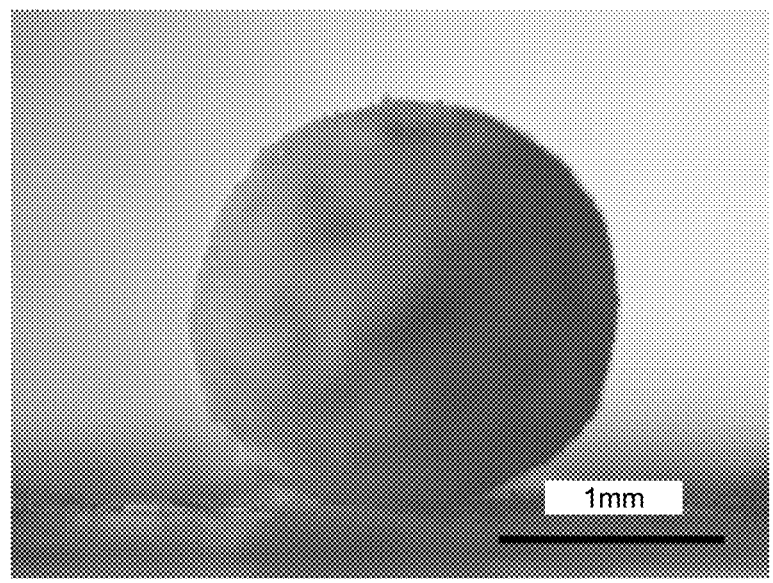
FIG. 4 is a microscopic photograph of a capsule obtained in Example 3.

Distilled water was used as a substance to be encapsulated, and polystyrene was used as a wall material polymer. Polystyrene (7.5% by weight) was dissolved in toluene. Distilled water was dispersed in the obtained polystyrene solution by adding 3 mL of distilled water to 7 mL of the polystyrene solution, followed by stirring. The obtained solution (10 mL) was added dropwise onto the marshmallow gel fine particle powder such that the marshmallow gel fine particle powder was sprinkled on the resulting droplets, thereby preparing polymer droplets which were entirely coated with the marshmallow gel fine particles (liquid marbles). The liquid marbles were put into a beaker having a bottom diameter of 30 mm, and were rotary-shaken at 200 rpm for 1 hour at 25° C., thereby evaporating toluene from the liquid marbles to solidify the polymer droplets. Thus, spherical solid capsules in which distilled water was encapsulated in polystyrene were obtained. FIG. 4 is a microscopic photograph of a capsule obtained in Example 3. The encapsulation efficiency of distilled water in the obtained capsules was 91±5%, and the particle size was 2 mm.

Example 4

Mononuclear (hollow) spherical capsules were prepared. Specifically, camphorquinone (1 mol %) and ethyl 4-(dimethylamino)benzoate (1 mol %) were dissolved in trimethylolpropane trimethacrylate. Droplets (8 μL) of the obtained solution were added dropwise onto the marshmallow gel fine particle powder, rolled on the powder such that the marshmallow gel fine particle powder was sprinkled on the droplets, thereby preparing monomer droplets which were entirely coated with the marshmallow gel fine particles (liquid marbles). Subsequently, 2 μL of distilled water was injected into the liquid marbles using a syringe needle without breaking the shape of each liquid marble, and the resulting droplets were put into a beaker having a bottom diameter of 30 mm, and the beaker was rotary-shaken at a predetermined shaking speed. After a lapse of a predetermined time period from the start of rotary shaking, LED light having a luminous flux of 24 W was irradiated for 1.5 minutes, thereby causing photopolymerization of the monomer to solidify the droplets. Conditions under which mononuclear capsules having a spherical shape and a uniform wall thickness could be prepared were selected by changing the rotary shaking speed (0 to 190 rpm) and the rotary shaking time (0 to 30 seconds) from the start of rotary shaking to light irradiation. It was evaluated whether or not the capsules were spherical based on the degrees of sphericity of the capsules obtained as follows.

Figure 5:
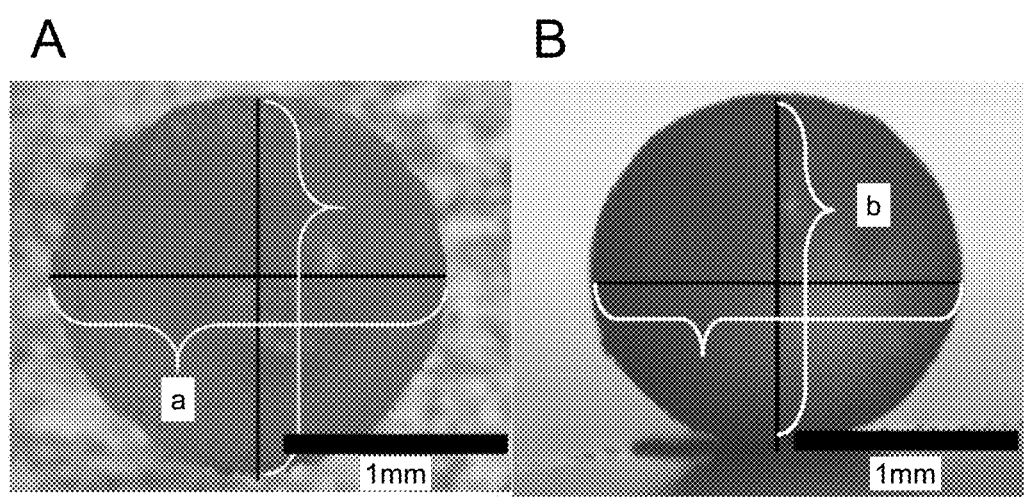
FIG. 5A is a microscopic photograph of one of the capsules obtained in Example 4 taken in the horizontal direction.
FIG. 5B is a microscopic photograph of one of the capsules obtained in Example 4 taken in the vertical direction.

Specifically, first, microscopic photographs of a capsule on the flat surface taken in the horizontal direction (when viewed from straight above) and in the vertical direction (when viewed end-on) were obtained. FIG. 5A is a microscopic photograph of one of the capsules obtained in Example 4 taken in the horizontal direction, and FIG. 5B is a microscopic photograph of one of the capsules obtained in Example 4 taken in the vertical direction. In each of the microscopic photographs taken from the horizontal and vertical directions of the capsule, the diameters of the portions shown in the figure were measured. The longest diameter was designated as "a" and the shortest diameter was designated as "b," and the degree of sphericity of the capsule was calculated by the following formula: sphericity (%)=shortest diameter b/longest diameter a×100. As the sphericity of the capsule was closer to 100%, the capsule has a shape closer to a true sphere, meaning that the capsule is more spherical. Table 2 shows the effects of the rotary shaking time until light irradiation and the rotary shaking speed on the sphericity of the capsule.

TABLE 2

| | Sphericity of capsules (%) | | | |
|---|---|---|---|---|
| Rotary shaking speed | Rotary shaking time until light irradiation (sec) | | | |
| (rpm) | 0 | 10 | 20 | 30 |
| 0 | 78 ± 3 | — | — | — |
| 130 | 96 ± 2 | 76 ± 7 | 73 ± 2 | 73 ± 3 |
| 150 | 92 ± 3 | 84 ± 10 | 75 ± 3 | 66 ± 4 |
| 190 | 82 ± 10 | 88 ± 4 | 84 ± 7 | 85 ± 4 |

Figure 6:
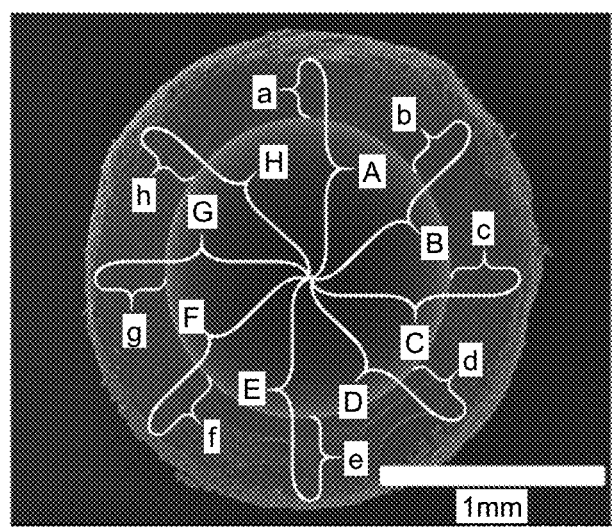
FIG. 6 is a microscopic photograph of a cross-section of one of the capsules obtained in Example 4.

The degree of uniformity of wall thickness was obtained as described below. First, a microscopic photograph of a cross-section of a capsule was obtained. FIG. 6 is a microscopic photograph of a cross-section of one of the capsules obtained in Example 4. As shown in FIG. 6, the ratios (a/A to h/H) of the wall thicknesses a to h to the capsule radii A to H were calculated at eight locations (A to H) in the cross-sectional view of the capsule, and the mean and standard deviation of their values were calculated. Subsequently, a coefficient of variation (standard deviation/mean) was obtained by dividing the standard deviation by the mean. The same operation was performed on 10 capsules, and the mean and standard deviation of the coefficient of variation were determined. The smaller the mean and standard deviation of the coefficient of variation, the more uniform the capsule wall thickness. Table 3 shows the effects of the rotary shaking time until light irradiation and the rotary shaking speed on the uniformity of the wall thickness of the capsule.

TABLE 3

| Rotary shaking speed (rpm) | Degree of uniformity of wall thickness | | | |
|---|---|---|---|---|
| | Rotary shaking time until light irradiation (sec) | | | |
| | 0 | 10 | 20 | 30 |
| 0 | 0.54 ± 0.08 | — | — | — |
| 130 | 0.17 ± 0.07 | 0.39 ± 0.17 | 0.59 ± 0.09 | 0.60 ± 0.06 |
| 150 | 0.25 ± 0.10 | 0.26 ± 0.19 | 0.37 ± 0.08 | 0.54 ± 0.08 |
| 190 | 0.36 ± 0.17 | 0.41 ± 0.16 | 0.29 ± 0.09 | 0.33 ± 0.10 |

Tables 2 and 3 showed that mononuclear spherical capsules, each of which was closest to a true sphere and more spherical and had the most uniform wall thickness, could be produced when the rotary shaking time until light irradiation was 0 second and the rotary shaking speed was 130 rpm.

REFERENCE SIGNS LIST

1: Monomer droplet or polymer droplet containing substance to be encapsulated
2: Solid fine particle
3: Microcapsule or microbead All publications, patents and patent applications cited in the present description are incorporated herein by reference in their entirety.

The invention claimed is:

1. A method for producing a mononuclear microcapsule or microbead, comprising:
   disposing a monomer droplet or polymer droplet containing a substance to be encapsulated, which has a surface coated with a plurality of solid fine particles, on a flat surface;
   solidifying the monomer droplet or polymer droplet disposed on the flat surface in a gas phase so as to form an outer shell of a capsule or microbead, wherein the outer shell consists of a polymer formed from the monomer droplet or polymer droplet, thereby forming a region enclosed by the outer shell, wherein the substance is encapsulated in the region, and
   removing the solid fine particles from the microcapsule or microbead.

2. The method for producing a mononuclear microcapsule or microbead according to claim 1, wherein the solidifying of the monomer droplet disposed on the flat surface in a gas phase comprises polymerizing the monomer droplet on the flat surface, and the solidifying of the polymer droplet disposed on the flat surface in a gas phase comprises removing a solvent in the polymer droplet.

3. The method for producing a mononuclear microcapsule or microbead according to claim 2, wherein the monomer is at least one selected from the group consisting of a (meth)acrylate, a styrene-based monomer, and divinylbenzene.

* * * * *